United States Patent
Scheller et al.

(10) Patent No.: US 8,075,553 B2
(45) Date of Patent: Dec. 13, 2011

(54) ILLUMINATED DIRECTIONAL LASER PROBE

(75) Inventors: Gregg D. Scheller, Glencoe, MO (US); Michael D. Auld, Flemington, NJ (US); Timothy J. Nadolski, Webster Groves, MO (US)

(73) Assignee: Synergetics, Inc., O'Fallon, MO (US)

( * ) Notice: Subject to any disclaimer, the term of this patent is extended or adjusted under 35 U.S.C. 154(b) by 875 days.

(21) Appl. No.: 12/063,512

(22) PCT Filed: Aug. 11, 2006

(86) PCT No.: PCT/US2006/031348
§ 371 (c)(1),
(2), (4) Date: May 16, 2008

(87) PCT Pub. No.: WO2007/021914
PCT Pub. Date: Feb. 22, 2007

(65) Prior Publication Data
US 2008/0287938 A1 Nov. 20, 2008

Related U.S. Application Data

(60) Provisional application No. 60/707,475, filed on Aug. 11, 2005.

(51) Int. Cl.
*A61B 18/20* (2006.01)
(52) U.S. Cl. .............................. 606/13; 606/15; 606/16
(58) Field of Classification Search ............... 606/2, 2.5, 606/4–7, 13–16, 78; 607/88, 89; 128/898
See application file for complete search history.

(56) References Cited

U.S. PATENT DOCUMENTS

| | | | |
|---|---|---|---|
| 4,347,837 A | 9/1982 | Hosono | |
| 4,674,497 A | 6/1987 | Ogasawara | |
| 4,744,360 A | 5/1988 | Bath | |
| 5,156,604 A | 10/1992 | Hessel et al. | |
| 5,172,685 A | 12/1992 | Nudelman | |
| 5,281,214 A | 1/1994 | Wilkins et al. | |
| 5,300,061 A | 4/1994 | Easley et al. | |
| 5,356,407 A * | 10/1994 | Easley et al. | 606/4 |
| 5,372,585 A | 12/1994 | Tiefenbrun et al. | |
| 5,469,524 A | 11/1995 | Esch et al. | |
| 5,512,034 A | 4/1996 | Finn et al. | |
| 5,520,222 A | 5/1996 | Chikama | |
| 5,603,710 A | 2/1997 | Easley et al. | |
| 5,656,011 A | 8/1997 | Uihlein et al. | |
| 5,688,264 A | 11/1997 | Ren et al. | |
| 5,735,792 A | 4/1998 | Vanden Hoek et al. | |

(Continued)

*Primary Examiner* — Ahmed Farah
(74) *Attorney, Agent, or Firm* — Evans & Dixon, LLC; Joseph M. Rolnicki (57) ABSTRACT

An ophthalmic surgery illuminated directional laser probe has a handle and a rigid tubular tip projecting from the handle, and has an illumination optic fiber and a laser optic fiber that extend through the handle and the tip. A mechanism on the handle is operable to extend distal ends of the illumination optic fiber and the laser optic fiber from the distal end of the instrument tip, and to retract the distal ends of the illumination optic fiber and the laser optic fiber back into the interior of the tip. At least one of the distal ends of the illumination optic fiber and the laser optic fiber is held in a curved configuration. The distal ends of the illumination optic fiber and the laser optic fiber are secured to each other, whereby both the illumination optic fiber and the laser optic fiber curve into a bent configuration as the distal ends of the illumination optic fiber and the laser optic fiber are extended from the distal end of the instrument tip.

26 Claims, 6 Drawing Sheets

U.S. PATENT DOCUMENTS

| | | |
|---|---|---|
| 5,741,225 A | 4/1998 | Lax et al. |
| 5,766,164 A | 6/1998 | Mueller et al. |
| 5,807,242 A | 9/1998 | Scheller et al. |
| 5,855,577 A * | 1/1999 | Murphy-Chutorian et al. .. 606/7 |
| 5,865,831 A | 2/1999 | Cozean et al. |
| 5,957,916 A | 9/1999 | Jeevanandam et al. |
| 5,993,072 A | 11/1999 | de Juan, Jr. et al. |
| RE36,473 E | 12/1999 | Esch et al. |
| 6,015,403 A | 1/2000 | Jones |
| 6,053,911 A | 4/2000 | Ryan et al. |
| 6,142,990 A | 11/2000 | Burk |
| 6,428,553 B1 | 8/2002 | Trese |
| 6,572,608 B1 | 6/2003 | Lee et al. |
| 6,575,989 B1 | 6/2003 | Scheller et al. |
| 6,984,230 B2 * | 1/2006 | Scheller et al. ............ 606/15 |
| 7,141,048 B1 | 11/2006 | Charles |
| 7,473,249 B2 * | 1/2009 | Scheller et al. ............ 606/15 |
| 2005/0154379 A1 | 7/2005 | McGowan et al. |

* cited by examiner

ILLUMINATED DIRECTIONAL LASER PROBE

This patent application claims the benefit of Provisional Patent Application Ser. No. 60/707,475, filed Aug. 11, 2005.

BACKGROUND OF THE INVENTION (1) Field of the Invention

The present invention pertains to a microsurgical apparatus primarily used in ophthalmic surgery procedures. In particular, the invention pertains to an illuminated directional laser probe having a handle and a rigid tubular tip projecting from the handle, and having an illumination optic fiber and a laser optic fiber that extend through the handle and the tip. A mechanism on the handle is operable to cause distal ends of the illumination optic fiber and the laser optic fiber to be extended from the distal end of the tubular tip, and to cause the distal ends of the illumination optic fiber and the laser optic fiber to be retracted back into the tubular tip. At least one of the distal ends of the illumination optic fiber and the laser optic fiber is held in a curved configuration. The distal ends of the illumination optic fiber and the laser optic fiber are secured to each other, whereby both the illumination optic fiber and the laser optic fiber curve into a bent configuration as the distal ends of the illumination optic fiber and the laser optic fiber are extended from the distal end of the tubular tip.

(2) Description of the Related Art

In ophthalmic surgery procedures, different types of instruments are available for use by the surgeon to transmit illumination light to a surgical site in the interior of the eye and to transmit laser energy to a surgical site in the interior of the eye. A typical ophthalmic surgery illuminator comprises a handle with a small tubular metal tip that projects from the handle. An illumination optic fiber, having a proximal end with a connector for coupling to a source of illumination light, passes through the handle and the tip of the instrument. The distal end of the optic fiber is positioned adjacent the distal end of the instrument tip and projects illumination light.

The typical ophthalmic surgery laser probe is constructed in basically the same manner as the illumination probe. The laser probe also has a handle with a small tubular metal tip projecting from the handle. A laser optic fiber, having a proximal end with a connector for coupling to a source of laser light, passes through the handle and the tip of the laser probe. The distal end of the laser optic fiber is positioned adjacent the distal end of the tip and projects laser light.

In use of an illumination optic fiber instrument and a laser optic fiber instrument in performing ophthalmic surgery procedures, it is necessary to provide two separate incisions in the eye. The distal end of the illumination instrument tip is inserted through one of the incisions to the eye interior and the distal end of the laser instrument is inserted through the other incision to the eye interior. Both the illumination instrument and the laser instrument are then manually manipulated to position their respective distal ends adjacent the surgical site in the interior of the eye. Illumination light provided by the distal end of the illumination instrument tip illuminates the surgical site, and laser light transmitted from the distal end of the laser instrument tip performs the surgical procedure.

The above-described ophthalmic surgery procedures are disadvantaged in that they require at least two incisions in the eye, increasing the trauma to the eye. Furthermore, the prior art illumination instrument and the prior art laser instrument described above are limited to directing illumination light and laser light to only the posterior area of the eye interior. In using instruments of this type, the optimal delivery of illumination light and laser light to a surgical site at an anterior or forward portion of the retina cannot be achieved.

SUMMARY OF THE INVENTION

The present invention is a microsurgical illuminated directional laser probe that overcomes disadvantages associated with the prior art illumination instrument and laser instrument by providing the illuminated directional laser probe with the ability to deliver both illumination light and laser light through a single incision into the interior of the eye. In addition, the probe of the invention is capable of directing illumination light and laser light to anterior or forward portions of the eye interior.

The microsurgical probe of the invention is an improvement over microsurgical instruments used in ophthalmic surgery such as those disclosed in the U.S. Pat. No. 6,572,608 titled "Directional Laser Probe," and U.S. Pat. No. 6,984,230 titled "Directional Laser Probe," both of which are incorporated herein by reference. The illuminated directional laser probe of the invention has much of the same basic construction as the probes described in the two above-referenced patents, and therefore the common structural features of the probes will not be discussed in detail herein.

The illuminated directional laser probe of the invention is basically comprised of a handle that has opposite proximal and distal ends. An interior bore passes through the handle, and a cavity is formed in a side of the handle. The cavity communicates with the handle interior bore.

A rigid tubular tip projects from a distal end of the handle. The tip is preferably constructed of surgical steel and has the dimensions of a syringe needle. An interior bore of the tip communicates with the interior bore of a handle.

An illumination optic fiber and a laser optic fiber extend side by side through the interior bore of the handle and the interior bore of the tip. The illumination optic fiber has a length with opposite proximal and distal ends. The proximal end is connected to an illumination connector that is adapted to be connected to a light source, and the distal end is positioned adjacent the distal end of the probe tip.

The laser optic fiber also has a length with opposite proximal and distal ends. The proximal end has a laser connector that is adapted to be connected to a separate laser light source, and the distal end is positioned adjacent the probe tip distal end. In a first embodiment of the invention, both the illumination optic fiber and the laser optic fiber are held stationary relative to the handle.

A finger actuator is mounted in the handle cavity for forward movement toward the handle distal end, and for opposite rearward movement toward the opposite proximal end of the handle. In the first embodiment of the instrument, the finger actuator is connected to the tip. Movement of the finger actuator in the rearward direction causes the tip distal end to move toward the handle distal end and causes distal end portions of the illumination optic fiber and the laser optic fiber to be extended from the tip distal end. Movement of the finger actuator in the forward direction causes the tip to be extended from the handle distal end and causes the distal ends of both the illumination optic fiber and the laser optic fiber to be retracted into the interior bore of the tip.

A connection is provided between the illumination optic fiber and the laser optic fiber adjacent the distal ends of the illumination optic fiber and the laser optic fiber. The connection prevents relative movement between the illumination optic fiber and the laser optic fiber adjacent their distal ends.

In one embodiment of the instrument, a first metal tube is provided on the illumination optic fiber adjacent the illumination optic fiber distal end, and a second metal tube is provided on the laser optic fiber adjacent the laser optic fiber distal end. The first and second tubes are connected together by spot welds positioned along the lengths of the first and second tubes. Alternative means of connecting the first and second tubes include adhesives, banding of the tubes together, and other equivalent means.

In addition, at least one, and possibly both, of the first tube and second tube are constructed of a shape memory material that is formed in a curved or bent configuration. An example of a shape memory material is nitinol. The curved configurations of both the first tube and second tube cause the respective illumination optic fiber and laser optic fiber to gradually move through a curved path as the finger actuator is moved toward the rearward position on the handle and the distal end portions of the illumination optic fiber and laser optic fiber are extended from the tip distal end. By spacing the welds or adhesive along the lengths of the first and second tubes, the connection between the illumination optic fiber and the laser optic fiber is prevented from breaking apart as the illumination optic fiber and laser optic fiber move through their curved configurations. When the finger actuator is moved toward the forward position causing the rigid tip to be extended from the handle, the tip causes the illumination optic fiber and laser optic fiber to be straightened as the distal ends of the illumination optic fiber and laser optic fiber are moved back into the interior bore of the tip.

In a second embodiment of the instrument, a single metal tube is provided on the illumination optic fiber adjacent the illumination optic fiber distal end, and on the laser optic fiber adjacent the laser optic fiber distal end. The single metal tube is the connection between the illumination optic fiber and the laser optic fiber that prevents relative movement between the illumination optic fiber and the laser optic fiber adjacent their distal ends. The single metal tube is constructed of a shape memory material that is formed in a curved or bent configuration. The curved configuration of the single metal tube causes the illumination optic fiber and the laser optic fiber to gradually move through a curved path as the finger actuator is moved toward the rearward position on the handle and the distal end portions of the illumination optic fiber and laser optic fiber are extended from the tip distal end. When the finger actuator is moved toward the forward position causing the rigid tip to be extended from the handle, the tip causes the illumination optic fiber and the laser optic fiber to be straightened as the distal ends of the illumination optic fiber and laser optic fiber are moved back into the interior of the tip.

In an alternative embodiment of the instrument, the bent portions of the first tube and second tube on the respective illumination optic fiber and laser optic fiber is replaced by a length of wire. The wire is constructed of the shape memory material and has a curved or bent configuration. The wire is secured to both the illumination optic fiber and the laser optic fiber to cause the fibers to be moved to curved or bent configurations in the same manner as the previously described embodiment.

In a still further alternative embodiment of the instrument, at least one or possibly both of the illumination optic fiber and laser optic fiber are constructed of a material that has shape memory properties. The fiber or fibers having the shape memory properties are formed in the curved or bent configuration. The shape memory property of the fiber or fibers causes both the illumination optic fiber and laser optic fiber to gradually bend through a curved or bent configuration as the fiber distal ends are extended from the tip distal end by movement of the finger actuator toward the rearward position on the handle. The illumination optic fiber and laser optic fiber are straightened by moving the finger actuator toward the forward position on the handle, which causes the tip distal end to be extended over the curved portions of the illumination optic fiber and laser optic fiber, straightening the two fibers.

Thus, the illuminated directional laser probe of the invention enables supplying both illumination light and laser light to a surgical site in the interior of an eye through only a single incision in the eye. The probe of the invention also provides the ability to direct the illumination light and laser light simultaneously to the interior of the eye, enabling accessing a surgical site on an anterior portion or forward portion of the eye interior.

DESCRIPTION OF THE DRAWINGS

Further features of the invention are set forth in the following detailed description of the preferred embodiments of the invention and in the drawing figures.

DETAILED DESCRIPTION OF THE PREFERRED EMBODIMENTS

As stated earlier, the microsurgical illuminated directional laser probe of the invention is an improvement over microsurgical instruments used in ophthalmic surgery such as those disclosed in the U.S. Pat. No. 6,572,608 titled "Directional Laser Probe," and U.S. Pat. No. 6,984,230 titled "Directional Laser Probe," both of which are incorporated herein by reference. The illuminated directional laser probe 10 of the invention has much of the same basic construction as the probes described in the two above-referenced patents, and therefore the common structural features of the probes will not be described in detail herein.

Figure 1:
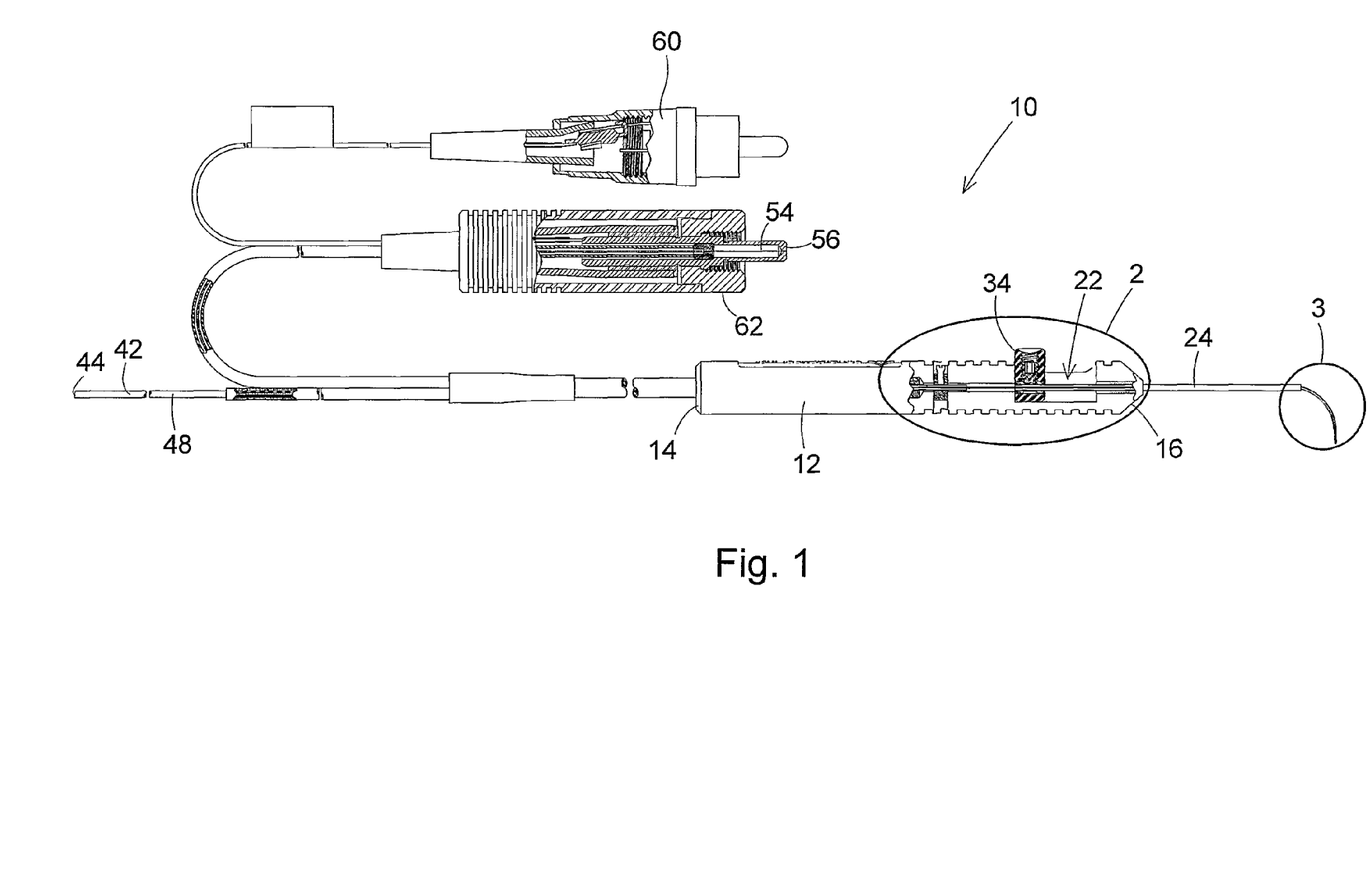
FIG. 1 is a side view, partially in section, of the illuminated directional laser probe of the invention.

The illuminated directional laser probe 10 of the invention is basically comprised of a handle 12 that has opposite proximal 14 and distal 16 ends. An interior bore 18 passes entirely through the handle. A cavity 22 is formed in a side of the handle and is positioned adjacent the handle distal end 16. The cavity 22 communicates with the handle interior bore 18.

A rigid tubular tip 24 projects from the handle distal end 16. The tip 24 is preferably constructed of surgical steel and has the dimensions of a syringe needle. The tip 24 has a straight length that extends between a proximal end 26 of the tip and a distal end 28 of the tip. The tip proximal end 24 is positioned in the handle cavity 22 and the tip distal end 24 is spaced outwardly from the handle distal end 16. An interior bore 34 extends entirely through the tip 24 and communicates with the handle interior bore 18. In this embodiment of the probe, the tip 24 is mounted in the handle bore 18 for sliding reciprocating movement of the tip 24 relative to the handle 12.

A finger actuator 34 is mounted in the handle cavity 22 for sliding reciprocating movement. The finger actuator 34 is mounted for forward movement in the cavity 22 toward the handle distal end 16, and for the opposite rearward movement in the cavity 22 toward the handle proximal end 14. The finger actuator 34 is connected to the tip proximal end 26 by a sleeve 36 that surrounds the tip proximal end 26 and by a set screw 38 that is screw threaded in the interior of the actuator 34. Thus, movement of the finger actuator in the rearward direction through the cavity 22 causes the tip 24 to slide through the handle bore 18 with the tip distal end 28 moving toward the handle distal end 16. Movement of the finger actuator in the forward direction through the handle cavity 22 causes the tip 24 to move relative to the handle 12 with the tip distal end 28 moving away from the handle distal end 16.

An illumination optic fiber 42 extends through the handle bore 18 and through the tip bore 32. The illumination optic fiber 42 has an elongate length that extends between a proximal end 44 of the fiber and an opposite distal end 46 of the fiber. The illumination optic fiber proximal end 44 is connected to an illumination connector 48 that is adapted to be connected to a light source that selectively supplies illumination light to the fiber proximal end 44. Connectors of this type are known in the art. The length of the illumination optic fiber 42 extends from its proximal end 44 through the handle interior bore 18 and through the tip interior bore 32 to the distal end 46 of the optic fiber positioned adjacent the distal end 28 of the tip. As in other optic fiber microsurgical instruments, a portion of the protective cladding of the illumination optic fiber 42 is removed adjacent the fiber distal end 46.

A laser optic fiber 54 also extends through the handle 12 and the tip 24 side by side with the illumination optic fiber 42. The laser optic fiber 54 also has an elongate length that extends between a proximal end 56 and a distal end 58 of the fiber. A laser light source connector 62 is connected to the proximal end 56 of the laser optic fiber 54. The laser light source connector 62 is connectable to a separate source of laser light that is transmitted through the laser optic fiber 54 from the fiber proximal end 56 to the fiber distal end 58. Laser light source connectors 62 of the type used with the probe 10 of the invention are known in the art. As in other optic fiber microsurgical instruments, a portion of the protective cladding of the laser optic fiber 54 is removed adjacent the fiber distal end 58. In the drawing figures, the distal end 58 of the laser optic fiber 54 is shown extending slightly beyond the distal end 46 of the illumination optic fiber 42. This is to allow the illumination light projected from the illumination optic fiber distal end 46 to illuminate an area of the surgical site being accessed by laser light transmitted from the laser optic fiber distal end 58. In alternate embodiments, the illumination optic fiber distal end 46 and the laser optic fiber distal end 58 can be positioned side by side.

A separate electrical connector 60 electrically communicates with the laser source connector 62. The electrical connector 60 is not needed for the operation of the illuminated directional laser probe 10, and therefore is not described further.

A first resilient tube 64 of resilient material is mounted on and contains at least a portion of the illumination optic fiber 42 adjacent the fiber distal end 46. The first tube 64 has a length that extends from a distal end 66 of the tube positioned adjacent the illumination optic fiber distal end 46, to an opposite proximal end 68 of the tube that is positioned in the handle 12. The length of the first tube 64 extends through the tip bore 32, the handle bore 18, and the handle cavity 22. The first tube proximal end 68 is secured stationary to the handle 12 by a set screw 72 that is screw threaded in the handle and engages against the first tube at its proximal end 68. The illumination optic fiber distal end 46 is secured to the first tube 64 by adhesives or other equivalent means, and thereby the illumination optic fiber 42 is held stationary relative to the handle 12 and to the tip 24.

A second tube of resilient material 74 is mounted on and contains at least a portion of the laser optic fiber 54 adjacent the laser optic fiber distal end 58. The second tube 74 has a length that extends between a distal end 76 of the second tube positioned adjacent the laser optic fiber distal end 58, to a proximal end 78 of the second tube that is positioned in the handle 12. Like the first tube 64, the length of the second tube 74 extends from the distal end 76 of the second tube, through the tip bore 32, the handle bore 18, and through the handle cavity 22. The second tube 74 is held stationary relative to the handle 12 and the tip 24 by the same set screw 72 that holds the first tube 64.

The exterior dimensions of the first tube 64 and the second tube 74 and the interior dimension of the tip bore 32 allow the tip 24 to slide easily over the exteriors of the two tubes 64, 74 as the finger actuator 34 is moved forwardly and rearwardly through the handle cavity 22.

Figures 2, 3, 4:
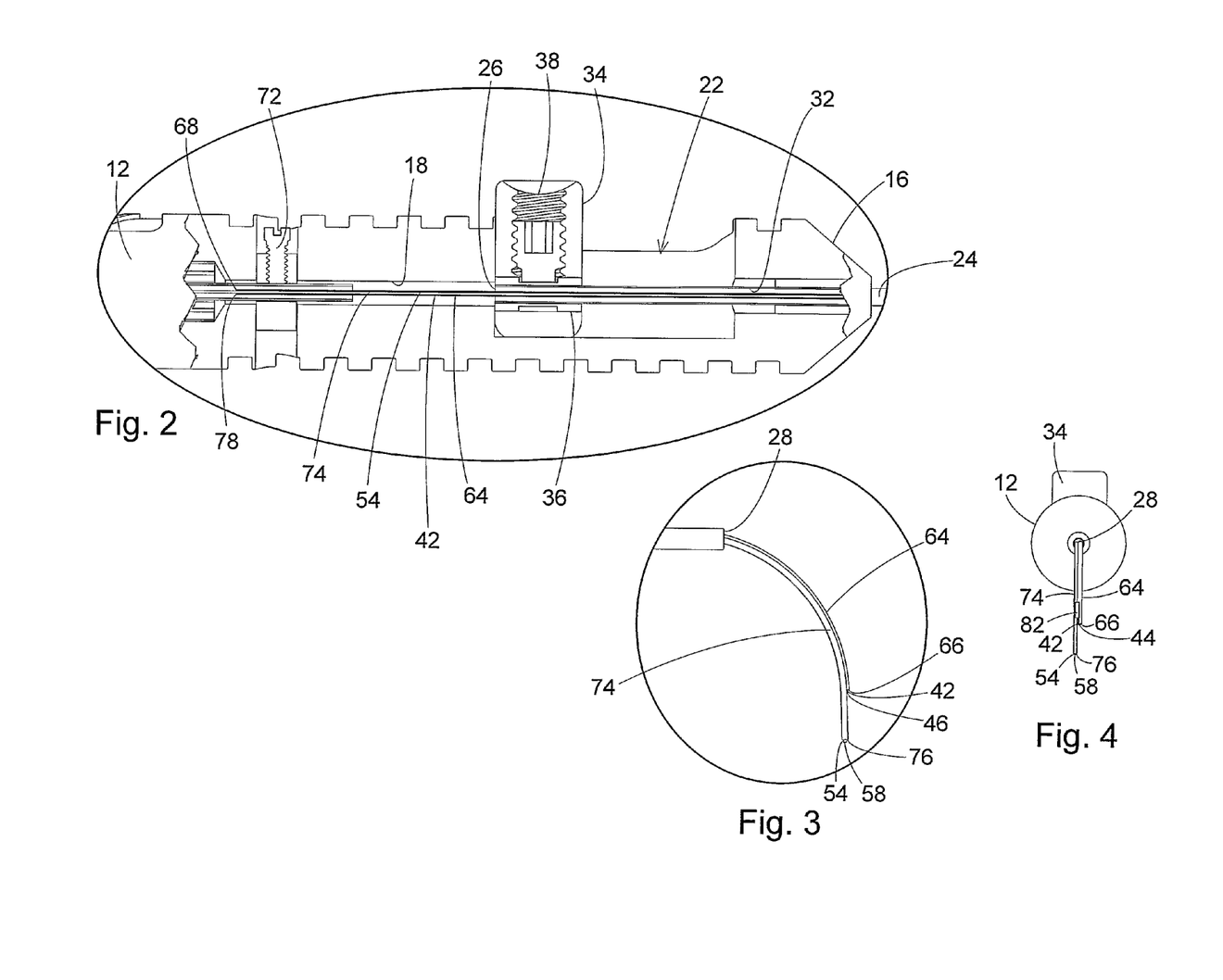
FIG. 2 is an enlarged partial view of a portion of the probe shown circled in FIG. 1.
FIG. 3 is an enlarged partial view of a portion of the probe shown circled in FIG. 1.
FIG. 4 is an end elevation view of the probe shown in FIG. 1.
Figure 5:
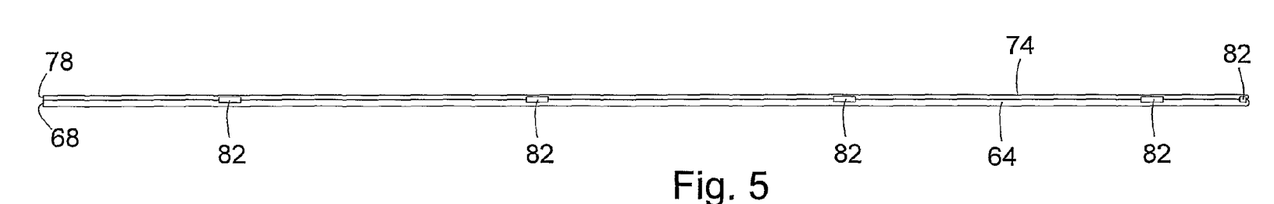
FIG. 5 is a plan view of the optic fibers of the probe removed from the probe.
Figures 6, 7:
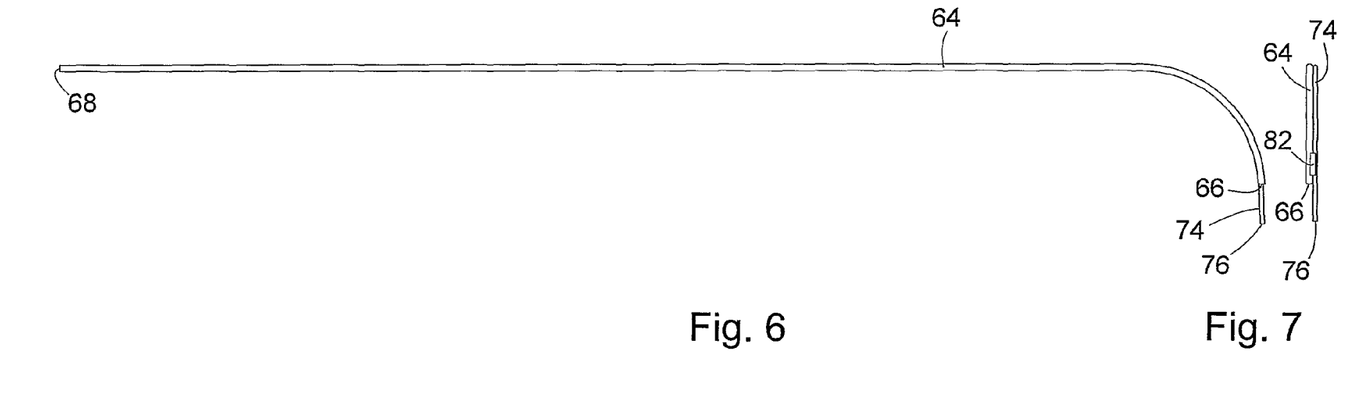
FIG. 6 is a side elevation view of the optic fibers shown in FIG. 5.
FIG. 7 is an end elevation view of the fibers shown in FIGS. 5 and 6.

In this embodiment of the invention, at least one of the first tube 64 and second tube 74, and possibly both of the tubes are constructed of a resilient shape memory material, for example the metal nitinol. The tube or tubes 64, 74 are formed in a bent or curved configuration adjacent their distal ends 66, 76. The resiliency of the material of the tubes 64, 74 allows the tubes to be straightened when a straightening force is exerted on the tubes, and then return to their bent or curved configurations when the straightening force is removed. FIGS. 1, 3, and 4 show the curved configurations of the first tube 64 and second tube 74 with portions of the tubes adjacent their respective distal ends 66, 76 projecting from the distal end 28 of the tip 24. The curved configurations of the tubes 64, 74 also bend portions of the illumination optic fiber 74 and the laser optic fiber 54 in curved configurations adjacent the respective distal ends 46, 58 of the fibers.

The illumination optic fiber 42 and the laser optic fiber 54 are connected together adjacent their respective distal ends 46, 58. The illumination optic fiber 42 and the laser optic fiber 54 are held together by a plurality of spot welds or brazing material 82 that connect the first tube 64 to the second tube 74. As shown in FIGS. 4-7, the spacial arrangement of the spot welds 82 along the length of the first tube 64 and second tube 74 connects the first and second tubes 64, 74 side by side, and prevents relative movement between the tubes. This also connects the illumination optic fiber 42 and the laser optic fiber 54 side by side adjacent their respective distal ends 46, 58, and prevents relative movement between the two fibers. The spacial arrangement of the spot welds 82 along the lengths of the two tubes 64, 74 allows the two tubes to resiliently bend between straight configurations and their curved configurations without breaking the connection between the two tubes provided by the spot welds 82.

In the operation of this first embodiment of the probe 10, movement of the finger actuator 34 in the rearward direction through the handle cavity 22 causes the tip distal end 28 to move toward the handle distal end 16. This causes the distal end portions of the illumination optic fiber 42 contained in the first tube 64 and the laser optic fiber 54 contained in the second tube 74 to be extended from the tip distal end 28. As the first tube 64 and second tube 74 extend outwardly from the tip distal end 28, the curved configurations of the tubes cause the illumination optic fiber 42 and the laser optic fiber 54 to gradually bend together toward the bent or curved configurations of the fibers shown in FIGS. 1, 3, and 4.

Movement of the finger actuator 34 in the forward direction through the handle cavity 22 causes the tip 24 to be extended from the handle distal end 16. This causes the first tube 64 containing the illumination optic fiber 42 and the second tube 74 containing the laser optic fiber 54 to be retracted into the tip 24 at the tip distal end 28. As the curved portions of the first tube 64 and second tube 74 are retracted into the tip interior bore 32, the rigid tip 24 straightens the curved or bent configurations of the two tubes. This causes the illumination optic fiber 42 and the laser optic fiber 54 to be gradually straightened as the two fibers are drawn back into the interior bore 32 of the rigid tip 24.

In variant embodiments of this first described probe 10, the spot welds 82 can be replaced by a plurality of spots of adhesive, or by an adhesive extending along portions of the first tube 64 and second tube 74 lengths. In addition, the spot welds 82 can be replaced by a plurality of bands connecting the first tube 64 to the second tube 74, or a single elongate tubular band that connects the two tubes.

A second embodiment of the illuminated directional laser probe is shown in FIGS. 8-15. The second embodiment of the probe 90 employs many of the same component parts of the previously described embodiment of the probe 10. The common parts are identified in FIGS. 8-15 with the same reference numbers employed in identifying the earlier described probe 10, with the reference numbers being followed by a prime ('). Because the same component parts of the two probes 10, 90 have been described previously, they will not be described again in describing the construction of the second embodiment of the probe 9 shown in FIGS. 8-15.

The primary difference between the probe 90 shown in FIGS. 8-15 and the previously described probe 10 is that the first tube 64 and second tube 74 are absent from the second embodiment of the probe 90. Instead, a single tube 92 surrounds and contains portions of the illumination optic fiber 42' and the laser optic fiber 54' adjacent the respective distal ends 46', 58' of the two fibers. The single tube 92 has a length with opposite proximal 94 and distal 96 ends. In the preferred embodiment of the invention, the single tube 92 is constructed of a resilient shape memory material, such as nitinol. The exterior dimension of the single tube 92 is just large enough to extend around and connect the illumination optic fiber 42' and the laser optic fiber 54' side by side, and still slide through the interior bore 32' of the tip 24'. As in the first tube 64 and second tube 74 of the first described embodiment of the probe, the single tube 92 has a bent or curved configuration adjacent the tube distal end 96. The curved configuration of the single tube 94 holds portions of the illumination optic fiber 42' and the laser optic fiber 54' in a bent or curved configuration adjacent the distal ends 46', 58' of the respective fibers. The resiliency of the material of the single tube 92 allows the curved portion of the tube to be straightened by the rigid tip 24', and then to resume the curved configuration when the curved portion is extended out of the tip 24'.

Figures 13, 14, 15:
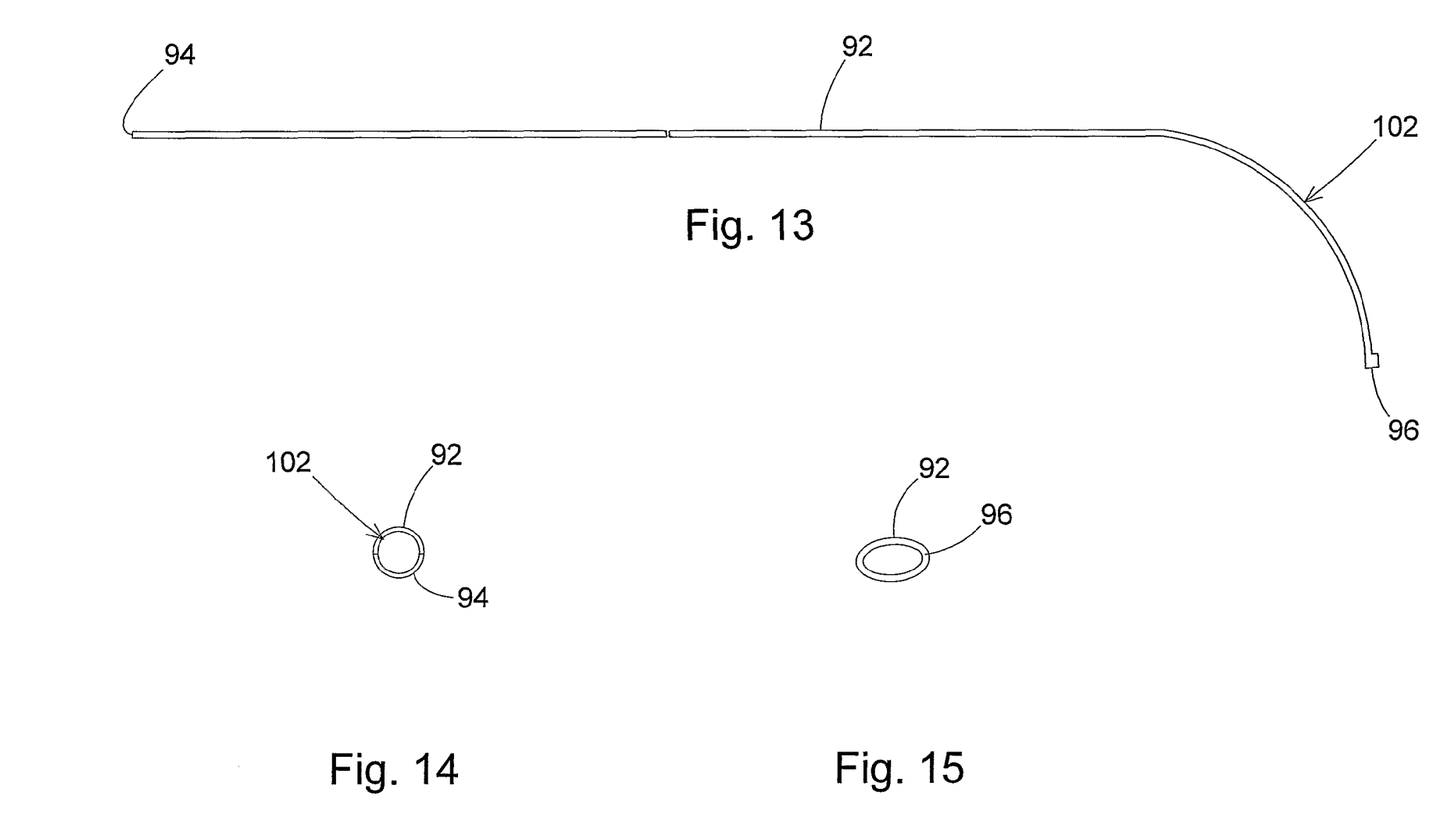
FIG. 13 is a side elevation view of a tube that connects the optic fibers of the probe of FIG. 8.
FIG. 14 is an end elevation view of the proximal end of the tube shown in FIG. 13.
FIG. 15 is an end elevation view of the distal end of the tube shown in FIG. 13.

FIGS. 14-15 show the single tube 92 removed from the probe 90, with the illumination optic fiber 42' and the laser optic fiber 54' removed from the tube. The single tube 92 has a generally oblong interior bore 98 adjacent the tube distal end 96. The bore 98 is dimensioned for containing and connecting the illumination optic fiber 42' and the laser optic fiber 74' adjacent their distal ends. As the single tube 92 extends from its distal end 96 toward its proximal end 94, an elongate notch 102 is formed in the side of the tube. The elongate notch 102 removes substantially half of the width or half of the side wall of the single tube 92. The notch 102 extends from adjacent the single tube distal end 96, along the entire length of the single tube 92 to the tube proximal end 94. The notch 102 increases the flexibility of the single tube 92 and allows the single tube to bend in its curved configuration shown in FIG. 10.

The elongate notch 102 forms a trough in the interior of the single tube 92 that contains a majority of the length of the illumination optic fiber 42' and the laser optic fiber 54'. The illumination optic fiber 42' and the laser optic fiber 54' are connected to the single tube 92 by an adhesive 104 applied in the interior of the single tube 92. The flexibility of the adhesive 104 and the elongate notch 102 allow the illumination optic fiber 42' and the laser optic fiber 54' to flex relative to the single tube 92 as the single tube 92 and the illumination optic fiber 42' and laser optic fiber 54' are moved through their bent or curved configurations shown in FIG. 10.

Figures 9, 10, 11, 12:
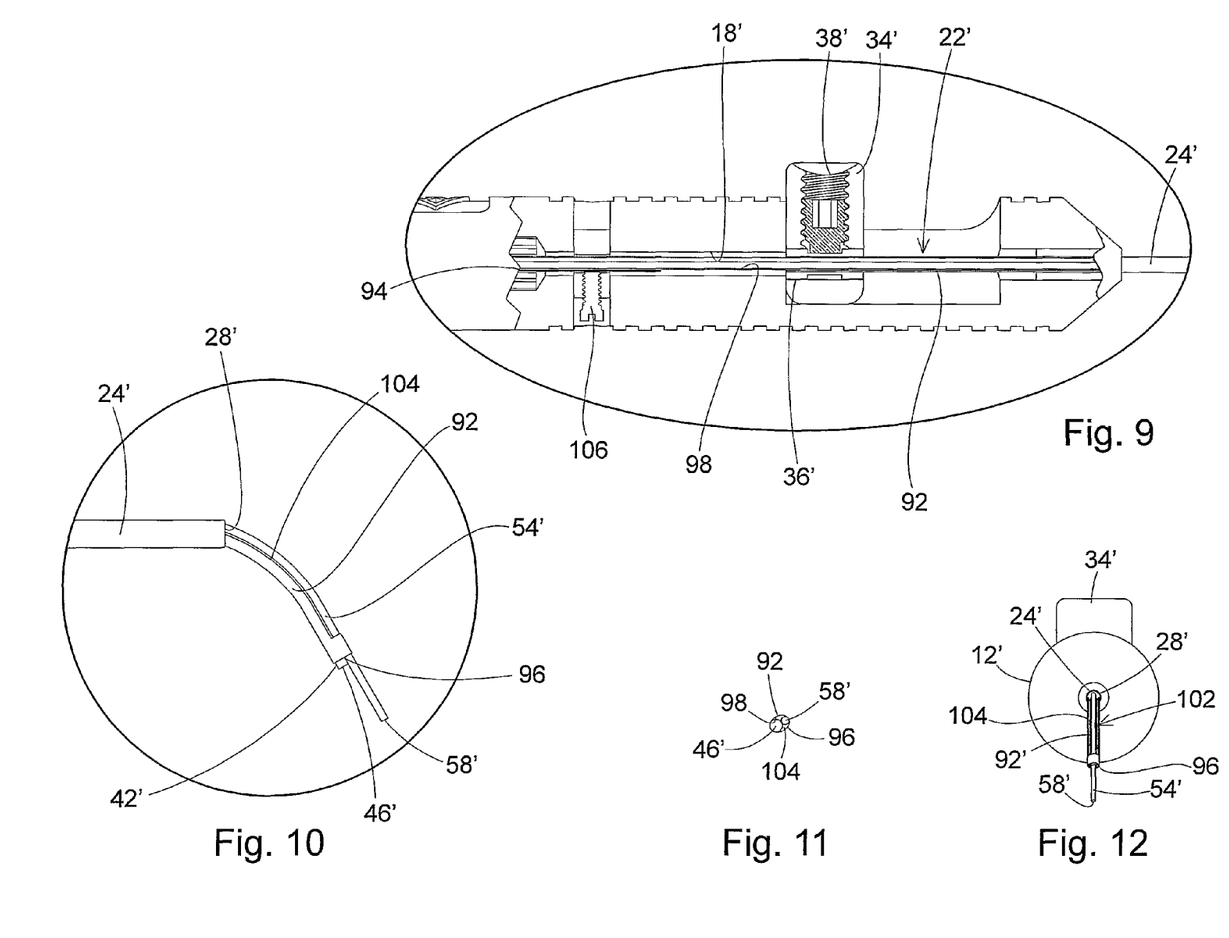
FIG. 9 is an enlarged partial view of a portion of the probe shown circled in FIG. 8.
FIG. 10 is an enlarged partial view of a portion of the probe shown circled in FIG. 8.
FIG. 11 is an end view of the optic fibers of the probe of FIG. 8.
FIG. 12 is an end elevation view of the probe of FIG. 8.

The elongate notch 102 is positioned on a side of the single tube 92 that is opposite the concave surface of the tube 92 formed when the tube is in the bent or curved configuration, as shown in FIG. 10. This positioning of the elongate notch 102 relative to the concave surface of the bent or curved single tube 92 also permits the connection between the tube 92 and the illumination optic fiber 42' and laser optic fiber 54' to flex as they are moved through their curved configurations, and prevents the illumination optic fiber 42' and/or laser optic fiber 54' from breaking free of the single tube 92 as the tube is moved through the curved configuration.

Figure 8:
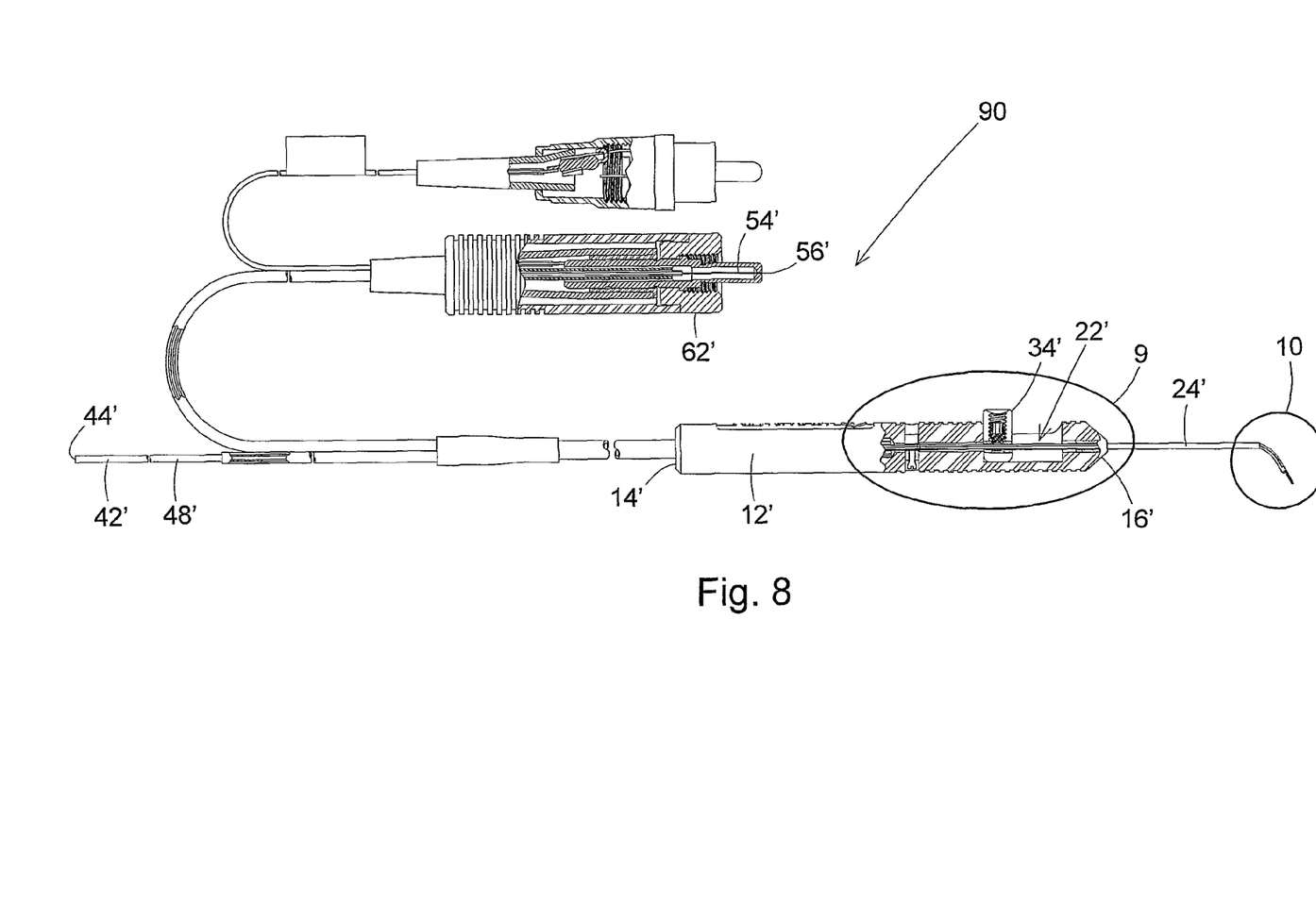
FIG. 8 is a side elevation view, partially in section, of a further embodiment of the illuminated directional laser probe.

The length of the single tube 92 extends from the tube distal end 96 through the tip interior bore 32', the handle cavity 22', and the handle interior bore 18' to the tube proximal end 94. The tube proximal end 94 is secured stationary to the illumination optic fiber 42' and the laser optic fiber 54', and to the handle 12' by a set screw 106 that is screw threaded into the handle 12' and engages against the side of the single tube 92 adjacent the tube proximal end 94. Thus, the single tube 92 and the illumination optic fiber 42' and laser optic fiber 54' are held stationary relative to the handle 12' and the tip 24'.

Operation of this embodiment of the probe 90 is substantially the same as that as the earlier described probe 10. Movement of the finger actuator 34' in the rearward direction causes the tip distal end 28' to move toward the handle distal end 16' and causes the distal end portions of the illumination optic fiber 42' and laser optic fiber 54' contained in the single tube 92 to be extended from the tip distal end 28'. This causes the portions of the illumination optic fiber 42' and the laser optic fiber 54' contained in the portion of the single tube 92 having the curved configuration to gradually bend in a curved configuration with the tube. Movement of the finger actuator 34' in the forward direction causes the rigid tip 24' to be extended from the handle distal end 16'. This moves the rigid tip 24' over the curved portion of the single tube 92, straightening the curvature of the tube 92 and the curvature of the illumination optic fiber 42' and the laser optic fiber 54' contained in the tube 92.

In still further alternate embodiments of the invention, the bent portions of the first tube 64, second tube 74, and single tube 92 are replaced by a length of wire having shape memory properties. The wire is secured to the illumination optic fiber and the laser optic fiber, and is provided with a curved portion that holds the two fibers in a curved configuration when the fibers and the curved portion of the wire are extended from the probe tip.

In a still further alternative embodiment of the instrument, at least one, or possibly both of the illumination optic fiber and laser optic fiber are constructed of a material that has shape memory properties. The fiber or fibers having the shape memory properties are formed in the curved or bent configuration and are held together by spots of adhesive or other equivalent means. The shape memory property of the fiber or fibers causes both the illumination optic fiber and laser optic fiber to gradually bend through a curved or bent configuration as the fiber distal ends are extended from the distal end of the tip by movement of the finger actuator toward the rearward position on the handle. The illumination optic fiber and laser optic fiber are straightened by movement of the finger actuator toward the forward position on the handle, which causes the tip distal end to be extended over the curved portions of the two fibers, straightening the two fibers.

In a still further embodiment of the invention, the finger actuator is connected to the illumination optic fiber and laser optic fiber and causes movement of the two fibers relative to the handle 12 and the tip 24. In this embodiment, the tip 24 is secured stationary relative to the handle 12. Movement of the finger actuator in the forward direction causes distal end portions of the illumination optic fiber and laser optic fiber to be extended from the tip distal end, causing the two fibers to move to their bent or curved configurations. Movement of the finger actuator in the rearward direction moves the two fibers back into the interior of the tip, causing straightening of the curved portions of the fibers.

All of the embodiments of the illuminated directional laser probe of the invention described above enable supplying both illumination light and laser light to a surgical site in the interior of an eye through only a single incision in the eye. The probes of the invention also provide the ability to direct the illumination light and laser light simultaneously to the interior of the eye, enabling accessing a surgical site on an anterior portion or forward portion of the eye interior.

Although the probe of the invention has been described above by reference to particular embodiments of the invention, it should be understood that modifications and variations could be made to the embodiments without departing from the intended scope of the claims.

What is claimed is:

1. A surgical instrument that provides both illumination light and laser light to a surgical site, the surgical instrument comprising:
   a manually manipulatable handle;
   a rigid tubular tip on the handle, the tip projecting from the handle to a distal end of the tip;
   an illumination optic fiber having a length with opposite proximal and distal ends, the illumination optic fiber extending through the handle and the tip to the illumination optic fiber distal end positioned adjacent the tip distal end;
   a laser optic fiber having a length with opposite proximal and distal ends, the laser optic fiber extending through the handle and the tip to the laser optic fiber distal end positioned adjacent the tip distal end;
   at least one connection connecting the illumination optic fiber and the laser optic fiber, the at least one connection preventing relative movement between the laser optic fiber and the illumination optic fiber;
   portions of the illumination optic fiber and the laser optic fiber being held in a bent configuration adjacent the distal ends of the illumination optic fiber and the laser optic fiber by the at least one connection between the illumination optic fiber and the laser optic fiber being positioned adjacent the distal ends of the illumination optic fiber and the laser optic fiber; and,
   a mechanism on the handle, the mechanism being operable to cause relative movement between the tubular tip distal end and the distal ends of the illumination optic fiber and the laser optic fiber, the relative movement being between retracted and extended positions of the illumination optic fiber and the laser optic fiber relative to the tubular tip distal end where in the retracted positions the portions of the illumination optic fiber and the laser optic fiber held in the bent configuration are contained in the tubular tip and straightened by the tubular tip and in the extended positions, the portions of the illumination optic fiber and the laser optic fiber held in the bent configuration are positioned outside the tubular tip.

2. The surgical instrument of claim 1, further comprising:
   an illumination source connector that is removably connectable to a separate source of illumination light is connected to the illumination optic fiber proximal end; and
   a laser source connector that is removably connectable to a separate source of laser light is connected to the laser optic fiber proximal end.

3. The surgical instrument of claim 1, further comprising:
   the at least one connection connecting the illumination optic fiber and the laser optic fiber is a weld.

4. The surgical instrument of claim 3, further comprising:
   the weld is one of a plurality of separate welds connecting the illumination optic fiber and the laser optic fiber.

5. The surgical instrument of claim 1, further comprising:
   the at least one connection connecting the illumination optic fiber and the laser optic fiber is an adhesive connection.

6. The surgical instrument of claim 1, further comprising:
   the at least one connection connecting the illumination optic fiber and the laser optic fiber is flexible tubing that contains the portions of both the illumination optic fiber and the laser optic fiber.

7. The surgical instrument of claim 1, further comprising:
   a length of tubing having a bent configuration extends over the illumination optic fiber adjacent the illumination optic fiber distal end and holds the illumination optic fiber and the laser optic fiber in the bent configuration.

8. The surgical instrument of claim 1, further comprising:
   a length of tubing having a bent configuration extends over the laser optic fiber adjacent the laser optic fiber distal end and holds the illumination optic fiber and the laser optic fiber in the bent configuration.

9. The surgical instrument of claim 1, further comprising:
   a bent length of wire is operatively secured to the illumination optic fiber and the laser optic fiber adjacent the distal ends of the illumination optic fiber and the laser optic fiber and holds the illumination optic fiber and the laser optic fiber in the bent configuration.

10. The surgical instrument of claim 1, further comprising:
    at least one of the illumination optic fiber and the laser optic fiber is formed with a pre-bent configuration that holds the distal ends of the illumination optic fiber and the laser optic fiber in the bent configuration.

11. The surgical instrument of claim 1, further comprising:
the mechanism being operatively connected to the tubular tip and being operable to cause movement of the tubular tip relative to the illumination optic fiber and to the laser optic fiber and to the handle.

12. The surgical instrument of claim 1, further comprising:
the mechanism being operatively connected to the illumination optic fiber and to the laser optic fiber and being operable to cause movement of the illumination optic fiber and the laser optic fiber relative to the tip and to the handle.

13. A surgical instrument that provides both illumination light and laser light to a surgical site, the surgical instrument comprising:
a manually manipulatable handle;
a rigid tubular tip on the handle, the tip projecting from the handle to a distal end of the tip;
an illumination optic fiber having a length with opposite proximal and distal ends, the illumination optic fiber extending through the handle and the tip to the illumination optic fiber distal end positioned adjacent the tip distal end;
a laser optic fiber having a length with opposite proximal and distal ends, the laser optic fiber extending through the handle and the tip to the laser optic fiber distal end positioned adjacent the tip distal end;
at least one connection connecting the illumination optic fiber and the laser optic fiber, the at least one connection preventing relative movement between the laser optic fiber and the illumination optic fiber;
the illumination optic fiber and the laser optic fiber being held in a bent configuration adjacent the distal ends of the illumination optic fiber and the laser optic fiber;
a mechanism on the handle, the mechanism being operable to cause relative movement between the tubular tip distal end and the distal ends of the illumination optic fiber and the laser optic fiber between retracted and extended positions of the illumination optic fiber and the laser optic fiber relative to the tubular tip distal end, where in the retracted positions the bent configuration of the illumination optic fiber and the laser optic fiber is contained in the tubular tip and straightened by the tubular tip and in the extended positions, the distal ends of the illumination optic fiber and the laser optic fiber are extended outside of the tubular tip and beyond the tubular tip distal end where the distal ends of the illumination optic fiber and the laser optic fiber held in the bent configuration are positioned outside the tubular tip;
a first metal tube containing the illumination optic fiber;
a second metal tube containing the laser optic fiber; and,
at least one weld connecting the first metal tube to the second metal tube and connecting the illumination optic fiber and the laser optic fiber preventing relative movement between the illumination optic fiber and the laser optic fiber.

14. The surgical instrument of claim 13, further comprising:
at least one of the first metal tube and the second metal tube having a bent configuration that holds the illumination optic fiber and the laser optic fiber in the bent configuration adjacent the distal ends of the illumination optic fiber and the laser optic fiber.

15. The surgical instrument of claim 14, further comprising:
the at least one weld being one of a plurality of welds spatially arranged along the first metal tube and second metal tube.

16. The surgical instrument of claim 14, further comprising:
the mechanism being operatively connected to the tubular tip and being operable to cause movement of the tubular tip relative to the illumination optic fiber and to the laser optic fiber and to the handle.

17. The surgical instrument of claim 14, further comprising:
the mechanism being operatively connected to the illumination optic fiber and to the laser optic fiber and being operable to cause movement of the illumination optic fiber and the laser optic fiber relative to the tip and to the handle.

18. A surgical instrument that provides both illumination light and laser light to a surgical site, the surgical instrument comprising:
a manually manipulatable handle;
a rigid tubular tip on the handle, the tip projecting from the handle to a distal end of the tip;
an illumination optic fiber having a length with opposite proximal and distal ends, the illumination optic fiber extending through the handle and the tip to the illumination optic fiber distal end positioned adjacent the tip distal end;
a laser optic fiber having a length with opposite proximal and distal ends, the laser optic fiber extending through the handle and the tip to the laser optic fiber distal end positioned adjacent the tip distal end;
at least one connection connecting the illumination optic fiber and the laser optic fiber, the at least one connection preventing relative movement between the laser optic fiber and the illumination optic fiber;
the illumination optic fiber and the laser optic fiber being held in a bent configuration adjacent the distal ends of the illumination optic fiber and the laser optic fiber;
a mechanism on the handle, the mechanism being operable to cause relative movement between the tubular tip distal end and the distal ends of the illumination optic fiber and the laser optic fiber between retracted and extended positions of the illumination optic fiber and the laser optic fiber relative to the tubular tip distal end, where in the retracted positions the bent configuration of the illumination optic fiber and the laser optic fiber is contained in the tubular tip and straightened by the tubular tip and in the extended positions, the distal ends of the illumination optic fiber and the laser optic fiber are extended outside of the tubular tip and beyond the tubular tip distal end where the distal ends of the illumination optic fiber and the laser optic fiber held in the bent configuration are positioned outside the tubular tip;
a first metal tube containing the illumination optic fiber;
a second metal tube containing the laser optic fiber;
a plurality of separate welds spatially arranged along the first metal tube and the second metal tube and connecting the first metal tube and the second metal tube, and thereby connecting the illumination optic fiber and the laser optic fiber and preventing relative movement between the illumination optic fiber and the laser optic fiber; and
at least one of the first metal tube and the second metal tube having a bent configuration that holds the illumination optic fiber and the laser optic fiber in the bent configuration adjacent the distal ends of the illumination optic fiber and the laser optic fiber.

19. The surgical instrument of claim 18, further comprising:

the mechanism being operatively connected to the tubular tip and being operable to cause movement of the tubular tip relative to the illumination optic fiber and to the laser optic fiber and to the handle.

20. The surgical instrument of claim 18, further comprising:

the mechanism being operatively connected to the illumination optic fiber and to the laser optic fiber and being operable to cause movement of the illumination optic fiber and the laser optic fiber relative to the tip and to the handle.

21. A surgical instrument that provides both illumination light and laser light to a surgical site, the surgical instrument comprising:

a manually manipulatable handle;

a rigid tubular tip on the handle, the tip projecting from the handle to a distal end of the tip;

an illumination optic fiber having a length with opposite proximal and distal ends, the illumination optic fiber extending through the handle and the tip to the illumination optic fiber distal end positioned adjacent the tip distal end;

a laser optic fiber having a length with opposite proximal and distal ends, the laser optic fiber extending through the handle and the tip to the laser optic fiber distal end positioned adjacent the tip distal end;

a single tube containing the illumination optic fiber and the laser optic fiber, the single tube connecting the illumination optic fiber and the laser optic fiber and preventing relative movement between the illumination optic fiber and the laser optic fiber, the single tube having a bent configuration and the illumination optic fiber and the laser optic fiber being held in a bent configuration adjacent the distal ends of the illumination optic fiber and the laser optic fiber by the single tube;

a mechanism on the handle, the mechanism being operable to cause relative movement between the tubular tip distal end and the distal ends of the illumination optic fiber and the laser optic fiber between retracted and extended positions of the illumination optic fiber and the laser optic fiber relative to the tubular tip distal end, where in the retracted positions the bent configuration of the illumination optic fiber and the laser optic fiber is contained in the tubular tip and straightened by the tubular tip and in the extended positions, the distal ends of the illumination optic fiber and the laser optic fiber are extended outside of the tubular tip and beyond the tubular tip distal end where the distal ends of the illumination optic fiber and the laser optic fiber held in the bent configuration are positioned outside the tubular tip.

22. The surgical instrument of claim 21, further comprising:

an adhesive is positioned inside the single tube and connects the single tube to the illumination optic fiber and to the laser optic fiber.

23. The surgical instrument of claim 22, further comprising:

the single tube has an elongate notch in a portion of the single tube having the curved configuration, the elongate notch exposing an interior of the single tube.

24. The surgical instrument of claim 23, further comprising:

the single tube having a concave surface on a portion of the tube having the curved configuration, and the notch in the single tube being positioned on an opposite side of the single tube from the concave surface.

25. The surgical instrument of claim 21, further comprising:

the mechanism on the handle being operatively connected to the tubular tip and being operable to cause movement of the tubular tip relative to the illumination optic fiber, the laser optic fiber, the handle, and the single tube.

26. The surgical instrument of claim 21, further comprising:

the mechanism on the handle being operatively connected to the single tube and being operable to cause movement of the illumination optic fiber, the laser optic fiber, and the single tube relative to the tip and to the handle.

* * * * *